(12) United States Patent
Yamagishi et al.

(10) Patent No.: US 6,965,243 B2
(45) Date of Patent: *Nov. 15, 2005

(54) CAPACITANCE SENSOR

(75) Inventors: Junichi Yamagishi, c/o Unirec Co., Ltd., 6-3, 2-Chome, Kaminarimon, Taito-ku, Tokyo 111-0034 (JP); Eikou Yo, Tokyo (JP)

(73) Assignees: Junichi Yamagishi, Tokyo (JP); Unirec Co., Ltd., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 10/394,563

(22) Filed: Mar. 21, 2003

(65) Prior Publication Data

US 2004/0183548 A1    Sep. 23, 2004

(51) Int. Cl.⁷ ............................................. G01R 27/26
(52) U.S. Cl. ........................ 324/658; 324/663; 324/686
(58) Field of Search ............................... 324/658, 663, 324/686

(56) References Cited

U.S. PATENT DOCUMENTS

| 3,635,082 A | * | 1/1972 | Prellwitz et al. | 73/861.04 |
| 4,487,057 A | | 12/1984 | Lutz | 73/40.5 |
| 4,965,206 A | | 10/1990 | Kell | 435/287 |
| 5,208,544 A | | 5/1993 | McBrearty et al. | 324/687 |
| 5,423,206 A | | 6/1995 | Hetzel | 73/61.7 |
| 6,545,488 B2 | * | 4/2003 | Yamagishi et al. | 324/672 |
| 6,655,221 B1 | * | 12/2003 | Aspelund et al. | 73/861.04 |
| 2003/0184317 A1 | | 10/2003 | Yamagishi | 324/663 |

FOREIGN PATENT DOCUMENTS

| JP | 57-125839 | 8/1982 |
| JP | 63-5462 | 1/1988 |
| JP | 1-93559 | 6/1989 |
| JP | 4-501463 | 3/1992 |
| JP | 4-258752 | 9/1992 |
| JP | 2001-21397 | 1/2001 |

* cited by examiner

Primary Examiner—Anjan Deb
Assistant Examiner—John Teresinski
(74) Attorney, Agent, or Firm—Jordan and Hamburg LLP

(57) ABSTRACT

To detect a variation of capacitance in a path of a piping and enable to decide a fluid state of a fluid substance flowing through the path in the piping, a capacitance sensor (15) includes a measuring electrode (33) and a grounding electrode (35) made of a conductive metallic film and wound around a path in the piping (1), with an insulator (17) in between. A shield member (23) covers the measuring electrode and grounding electrode, with an insulator in between. The grounding electrode is narrower than the measuring electrode, and the measuring electrode and the grounding electrode are alternately disposed and are wound to be spiral along a flow direction.

4 Claims, 8 Drawing Sheets

CAPACITANCE SENSOR

BACKGROUND OF THE INVENTION

1. Field of the Invention

The present invention relates to a capacitance sensor.

2. Description of the Related Art

A piping fluid decision device decides a fluid state of the fluid in a piping for sending fluid. An example of the piping fluid decision device, as shown in FIG. 1, includes a piping 101 for sending fluid, electrodes 103 and 105 inserted in the piping 101. The device is arranged at, for example, a beer factory or food shop, and decides a fluid state of beer as fluid. The device detects a conductivity in the piping 101 using the electrodes 103 and 105, and detects a difference of conductivity between a liquid part 109 and a froth part 111 of the beer 107; as a result, the device decides the fluid state of the beer 107 flowing in the piping 101. Depending on a result of the deciding, the froth part 111 of the beer 107 flowing in the piping 101 is wasted, as necessary, to surely take out the liquid part 109 of the beer 107.

According to the device, it is possible to take out the beer 107 with little froth anytime from a take-out machine installed at a terminal of the piping 101.

The device mentioned above, however, has some problems. The electrodes 103 and 105 are inserted in the piping, so that beer 107 flowing in the piping 101 directly contacts the electrodes 103 and 105. This corrodes the electrodes 103 and 105 to causes a sanitary problem. The device detects a variation of conductivity between the liquid part 109 and the froth part 111, so that voltage variations to be small are necessarily integrated, with an increased calculation amount. The detection of conductivity tends to be influenced by an associated magnetic field, as the result it is impossible to dispose the device in a vicinity of an electromagnetic valve.

If the fluid substance such as water flowing in the piping 101 includes a plurality of solid bodies such as metal, soil, or stone and is formed a solid fluid substance such as a metallic flow, soil flow, or stone flow, the fluid substance may collide on the electrodes 103 and 105 electrodes are kept from collision with the fluid substance. This causes the electrodes 103 and 105 to be damaged, and a failure of detection. Therefore, it is difficult, for the device having electrodes 103 and 105 inserted in a piping 101 shown as FIG. 1, to make a decision on a fluid state of the fluid substance including a plurality of solid bodies.

SUMMARY OF THE INVENTION

An object of the present invention is to provide a capacitance sensor, capable of making a decision on a fluid state of a fluid substance flowing in a piping, irrespective of the kind, by detection variation of capacitance.

A first aspect of the present invention provides a capacitance sensor having a measuring electrode and a grounding electrode made of a conductive metallic film and wound around a path in the piping, with an insulator in between. A shield member covers the measuring electrode and grounding electrode, with an insulator in between. The grounding electrode is narrower than the measuring electrode, and the measuring electrode and the grounding electrode are alternately disposed and are wound to be spiral along a flow direction.

According to the first aspect, a variation of capacitance of the path in the piping can be detected by a measuring electrode and a grounding electrode of the conductive metallic film wound in turns. Therefore, a fluid state of a fluid substance in the path can be surely and easily decided, and sanitary conditions in the path also be maintained.

For example, a fluid substance may be flowed through the path in the piping, and a variation of capacitance of the path in the piping is detected. A reference variation of capacitance of the path is stored in advance to provide for a decision a fluid state of the fluid substance flowing through the path. The fluid state of the fluid substance flowing through the path can be decided by comparing the detected variation of capacitance and the stored variation of capacitance.

Accordingly, a decision can surely be made of a fluid state in a piping, for example, such as on a normality or abnormality or of a change of kind of fluid substance. Moreover, the fluid state of the fluid substance flowing through the path in a piping can be decided with non-contact manner, securing a sanitary condition even if the fluid substance is a food. The fluid state of the fluid substance flowing in the path can be decided by capacitance or its variation, with large voltage variation without needing an integration of detected values, and with a reduced calculation amount. The fluid state is detected by capacitance or its variation, so that it hardly receives influences of a magnetic field. Even if the fluid substance includes a plurality of solid bodies such as metal, soil, or stone and is formed a solid fluid substance such as a metallic flow, soil flow, or stone flow, electrodes are kept from collision with the fluid substance. Therefore, the fluid state of the fluid substance including a plurality of solid bodies can be surely and easily decided.

According to this aspect of the invention, the grounding electrode is narrower than the measuring electrode and the measuring electrode and the grounding electrode are alternately disposed. Therefore, the fluid state of the fluid substance flowing in the piping can be decided in a more ensured manner.

According to this aspect of the invention, the measuring electrode and the grounding electrode are wound to be spiral along a flow direction. Therefore, the fluid state of the fluid substance flowing in the piping can be decided in a more ensured and facilitated manner.

DETAILED DESCRIPTION OF EMBODIMENTS

Figure 1:
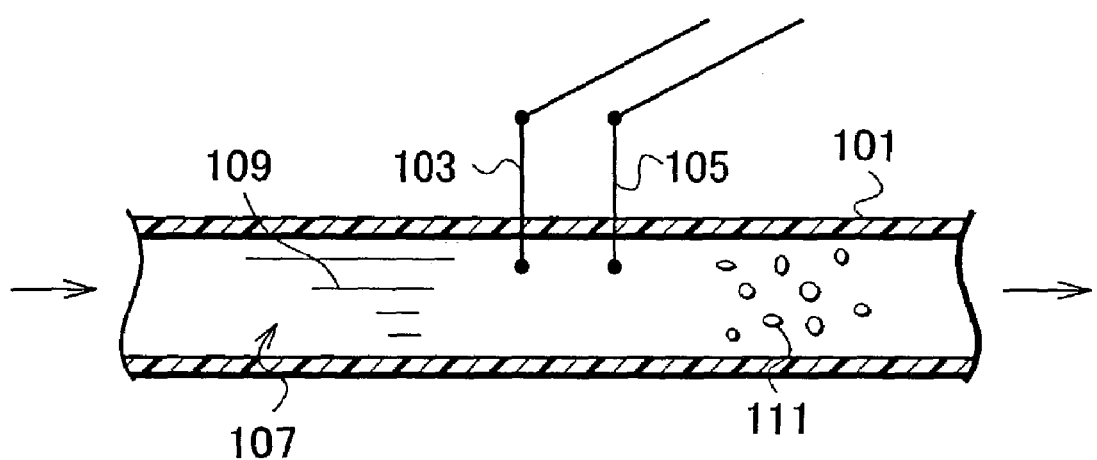
FIG. 1 is a schematic fragmentary illustration for explanation of a conventional piping fluid decision device.
Figure 2:
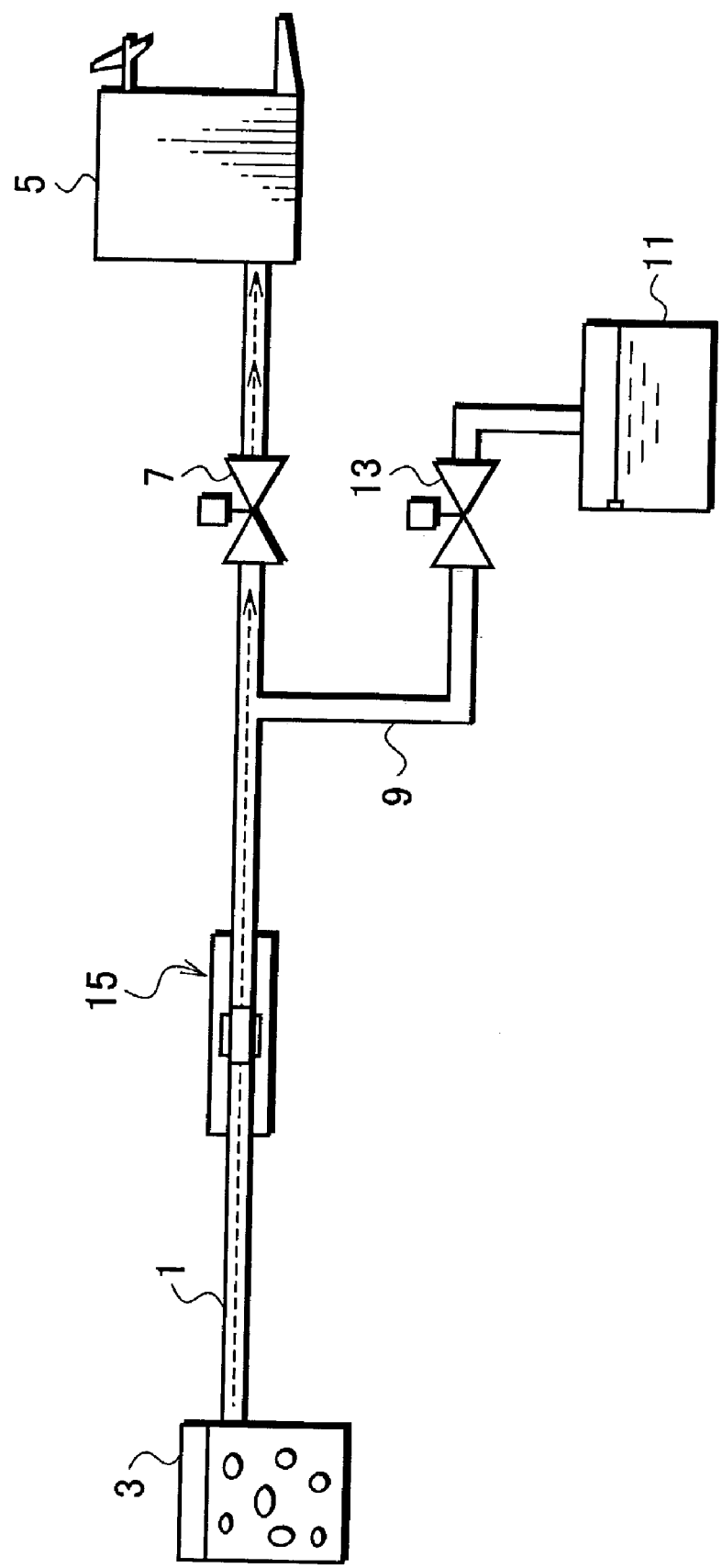
FIG. 2 is a schematic constitutional diagram of a piping fluid control system applying a capacitance sensor according to an embodiment of the present invention.

FIG. 2 is a schematic constitutional diagram of a piping fluid control system applying a capacitance sensor according to an embodiment of the present invention. According to this embodiment, a piping 1 is adapted as illustrated to conduct a fluid substance, for example beer, to be sent through an inside path thereof.

The piping 1 is connected at one end thereof to a beer tank 3, and at the other end to a beer take-out machine 5 serving as a substance take-out machine. On the way to the beer take-out machine 5 end of the piping 1 is provided with a first electromagnetic open-close valve 7, which is an adjust means as a first open-close valve to be interposed between a position of the substance take-out machine and a position of a later described capacitance sensor. The first electromagnetic open-close valve 7 allows controlling a fluid state of beer as a fluid substance flowing the path in the piping 1. That is, when the first electromagnetic open-close valve 7 is opened, beer of the piping 1 is sent to the beer take-out machine 5. When the first electromagnetic open-close valve 7 is closed, the sending of beer to the beer take-out machine 5 is stopped.

To the piping 1 is connected a drain pipe 9 serving as branch pipe upstream of the first electromagnetic open-close valve 7, to be interconnected between the position of the first open-close valve and the position of the capacitance sensor to be later-described. At a terminal of the drain pipe 9 is provided a drain tank 11. On the drain pipe 9 is installed a second electromagnetic open-close valve 13, which is a adjust means as a second open-close valve to be provided for the drain pipe 9.

If the second electromagnetic open-close valve 13 is opened when the first electromagnetic open-close valve 7 is closed by later-described control, beer (mainly froth) of the path in the piping 1 is discharged into the tank 11. If the first electromagnetic open-close valve 7 is opened and the second electromagnetic open-close valve 13 is closed, the discharge of the froth of beer from the piping 1 to the tank 11 stops.

Figure 3:
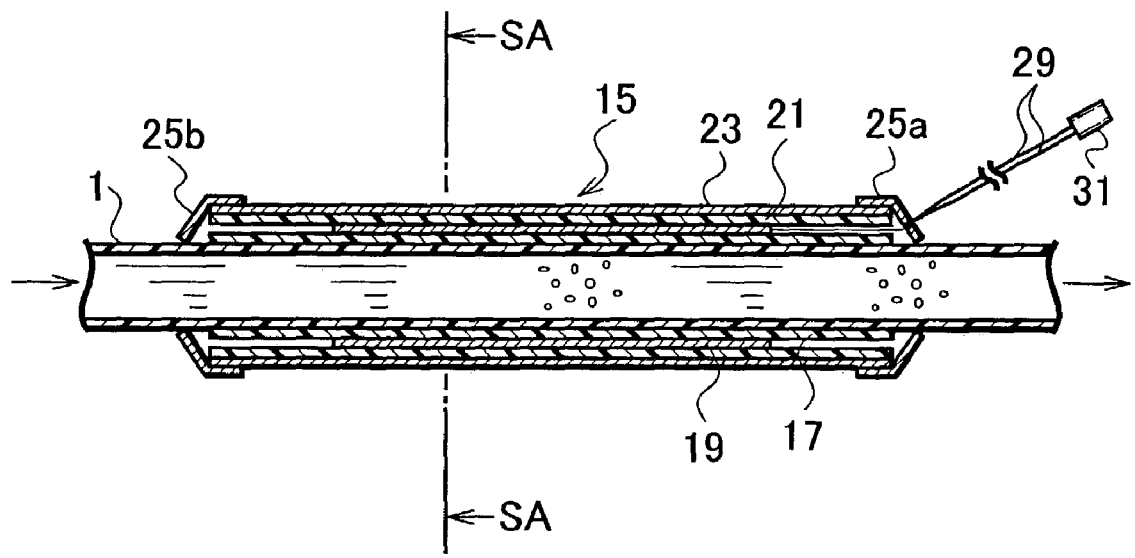
FIG. 3 is a sectional view of a sensor unit and associated parts of the embodiment.
Figure 4:
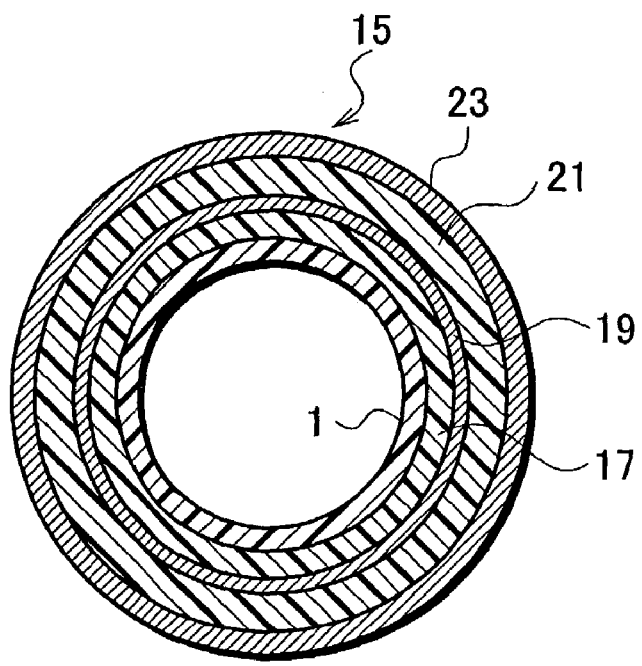
FIG. 4 is a detailed section along line SA—SA of FIG. 3.
Figure 5:
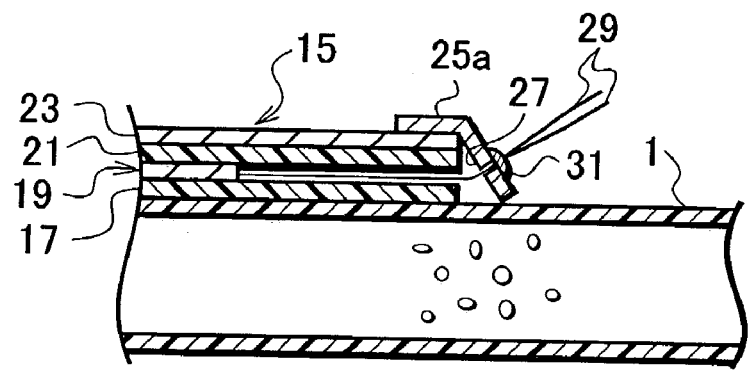
FIG. 5 is a detailed section of an essential part of the sensor unit of FIG. 3.

FIG. 3 is a sectional view of a sensor unit 15 and associated parts of the embodiment, FIG. 4 is a detailed section along line SA—SA of FIG. 3, FIG. 5 is a detailed section of an essential part of the sensor unit 15 of FIG. 3.

Outside the piping 1 is fit a sensor unit 15 serving as capacitance sensor which is adapted to detect variations of a capacitance of the path in the piping 1. The sensor unit 15 is constituted with an electrode 19 wound on an outside of the piping 1 defining the path, with an inner insulator 17 in between.

According to this embodiment, the insulator 17 is made of, for example, a vinyl chloride pipe. The insulator may be made of quartz glass, by moulding resin, or the like. The insulator 17 is tight fit on an outside circumference of the piping 1. An adhesive or the like may be used for a fixing in place of the fitting. By use of the vinyl chloride pipe as the insulator 17, the sensor unit 15 can be handled integrally to facilitate to be fit to the piping 1.

The piping 1 is made of an insulating material such as insulating resin, for example vinyl chloride. The piping 1 may be made of quartz glass as the insulating material, and may be made of the insulating material at least at a position thereof corresponding to the sensor unit 15.

The electrode 19 is made of a conductive metallic sheet such as a copper film to be configured as later-described. Outside the electrode 19 is provided a shield member 23, with an outer insulator 21 in between. The insulator 21 also is made of a pipe made of vinyl chloride. The insulator 21 tight covers the outside of the electrode 19. The insulator 21 may be made of quartz glass, or by moulding resin.

According to this embodiment, the shield member 23 is made of an aluminum pipe. The shield member 23 is tight fit on an outside of the insulator 21. End shield members 25a and 25b are fixed to both ends of the shield member 23 respectively. The end shield members 25a and 25b are made of aluminum.

One end shield member 25a is formed with a through hole 27 for drawing out lead wires 29 of the electrode 19. Between the shield member 25a and the lead wires 29 is filled with a resin mould 31. The lead wires 29 are provided with connectors 32 for external connection at their ends.

Figure 6:
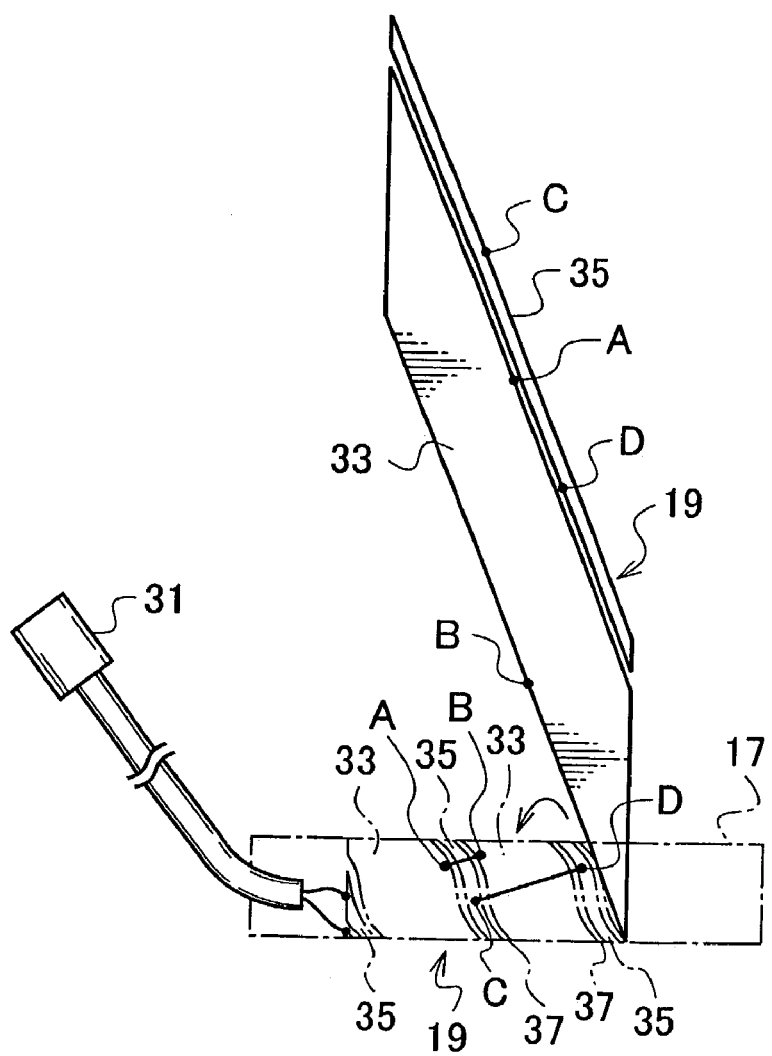
FIG. 6 is an illustration of an electrode being wound of the embodiment.

FIG. 6 is an illustration of the electrode 19 being wound. In FIG. 6, the electrode 19 is shown by one-dot-chain lines, as it is wound on the insulator 17 of vinyl chloride pipe, or by solid lines, as it is developed. The electrode 19 includes a measuring electrode 33 and a grounding electrode 35. Both the electrodes 33 and 35 are made of substantially parallelogram belt-shaped copper film. A sum of lengths of the short sides (left or right vertical sides in solid line in FIG. 6) of the electrodes 33 and 35 and a later-described gap 37 between the electrodes 33 and 35 is substantially equal to the length of an outside circumference of the insulator 17.

The grounding electrode 35 is narrower than the measuring electrode 33. The measuring electrode 33 as well as the grounding electrode 35 is wound on the out side circumference of the insulator 17 in a spiral form along a flow direction as shown by one-dot-chain lines, and fixed by use such as of an adhesive. The number of turns in this embodiment is about three rounds along the outside circumference of the insulator 17. As long as a variation of capacitance is detectable over an entire circumference of the piping 1 by the electrodes 33 and 35, the number of turns may be optionally selected. The electrode 19 has a gap 37 between the electrodes 33 and 35 wound on the insulator 17.

The electrodes 33 and 35 are alternately disposed, when wound on the insulator 17. In this condition, neighboring wound parts of the electrode 33 are mutually short-circuited between short-circuit points A and B. In the case of the electrode 35, neighboring wound parts are mutually short-circuited between short-circuit points C and D. In the wound condition of the electrode 19 in FIG. 6, the short-circuit points A, B, C, and D are positioned on the same side for convenient concurrent illustration, while actually the short-circuit points A, B, C, and D are located on positions shown in the developed state.

Figure 7:
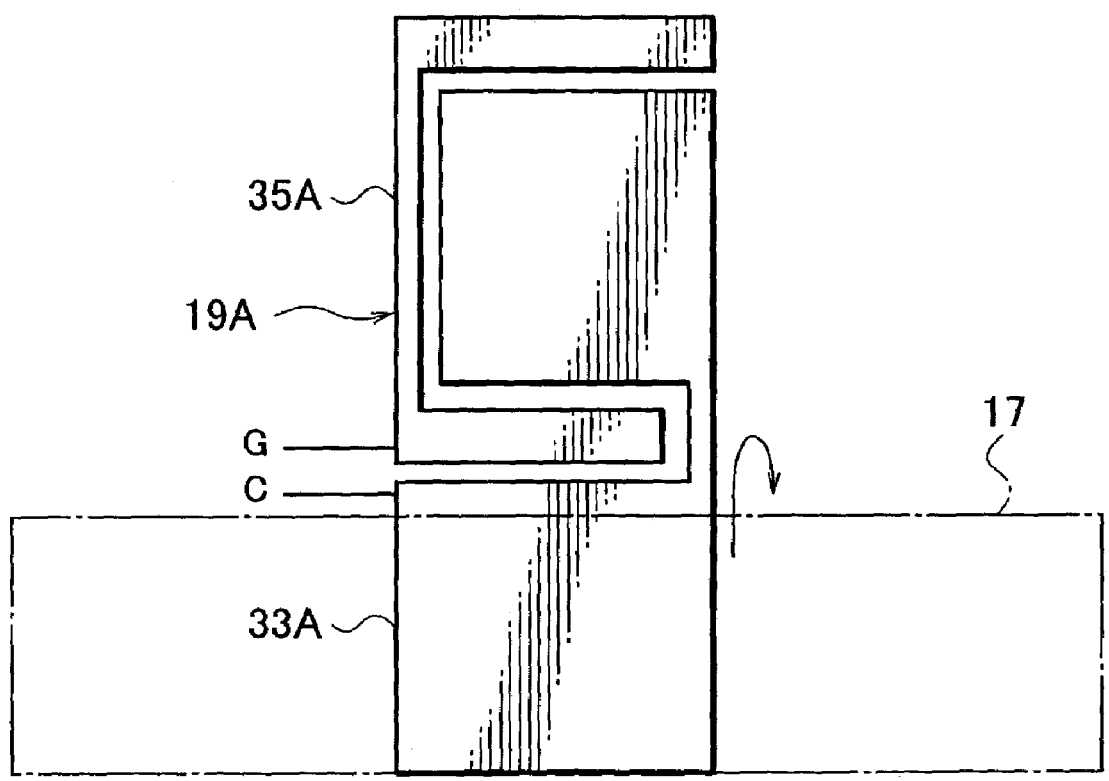
FIG. 7 is an exploded view of an electrode corresponding to the electrode of FIG.

Such arrangement provides an electrode constitution analogous in disposition to an electrode 19A of FIG. 7, for example. In the electrode 19 of FIG. 6, the short-circuit positions A, B, C, and D correspond in position to points A1, B1, C1, and D1 in the electrode 19A. The electrode 19 employs the constitution of the substantially parallelogram belt-shaped electrodes 33 and 35 short-circuited at the short-circuit point A, B, C, and D. Therefore, it is allowed for the electrode 19 to be spirally wound on the outside of the insulator 17.

It is also possible as a matter of course to use arrangement of the electrode 19A of FIG. 7 in place of the electrode 19. In FIG. 7, the electrode 19A includes a measuring electrode 33A and a grounding electrode 35A both wound around a whole circumference on an outside of the insulator 17. The electrodes 19 and 19A of FIG. 6 and FIG. 7 are different from each other. The difference is that the electrode 19 spirally wound on an outside of the insulator 17 as shown in FIG. 6, variation of capacitance due to a flow of a fluid substance such as beer in the path of the piping 1 can be detected more correctly and easily than the electrode 19A.

Figure 8:
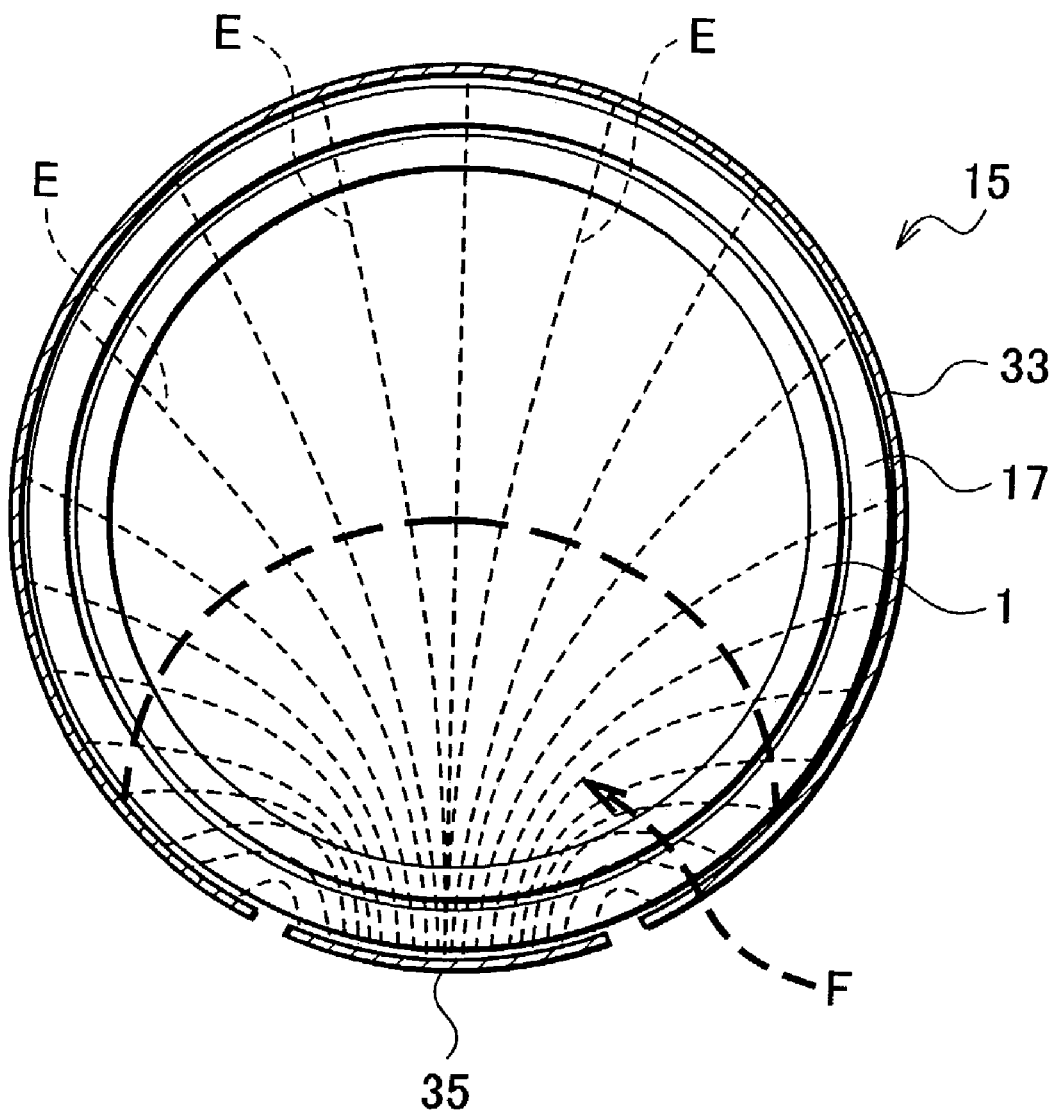
FIG. 8 is a schematic sectional view of the piping with a grounding electrode and measuring electrode of the capacitance sensor of the embodiment

FIG. 8 is a schematic sectional view of the piping 1 with a grounding electrode 35 and measuring electrode 33 of the capacitance sensor of this embodiment. In FIG. 8, the insulator 21 and the shield member 23 are not shown. According to the sensor unit 15 serving as the capacitance sensor, the grounding electrode 35 is narrower than the measuring electrode 33. Therefore, if the grounding electrode 35 was positioned near the lower portion of the piping 1, sensitivity-curved lines E forms a high sensitivity area F for the sensitivity-curved lines E in the lower portion of the piping 1 adjacent to the grounding electrode 35. Thus, when the grounding electrode 35 and measuring electrode 33 are alternately disposed and are wound to be spiral along a flow direction, the high sensitivity area F is distributed around the circumference of the piping 1 and formed in a 360 degree range. Accordingly, the sensor unit 15 can accurately make detection of capacitance of the piping 1 with the high sensitivity area F formed in the 360 degree range.

Furthermore, a capacitance sensor with a grounding electrode and measuring electrode having similar widths will have a relatively larger capacitance than the sensor unit 15 with the measuring electrode 33 of width substantially larger than the width of the grounding electrode 35. As a result, the capacitance sensor with a grounding electrode and measuring electrode having similar widths has a greater sensitivity to noise than the sensor unit 15 with the measuring electrode 33 of width substantially larger than the width of the grounding electrode 35. Thus, the sensor unit 15 can make detection with greater accuracy.

Figure 9:
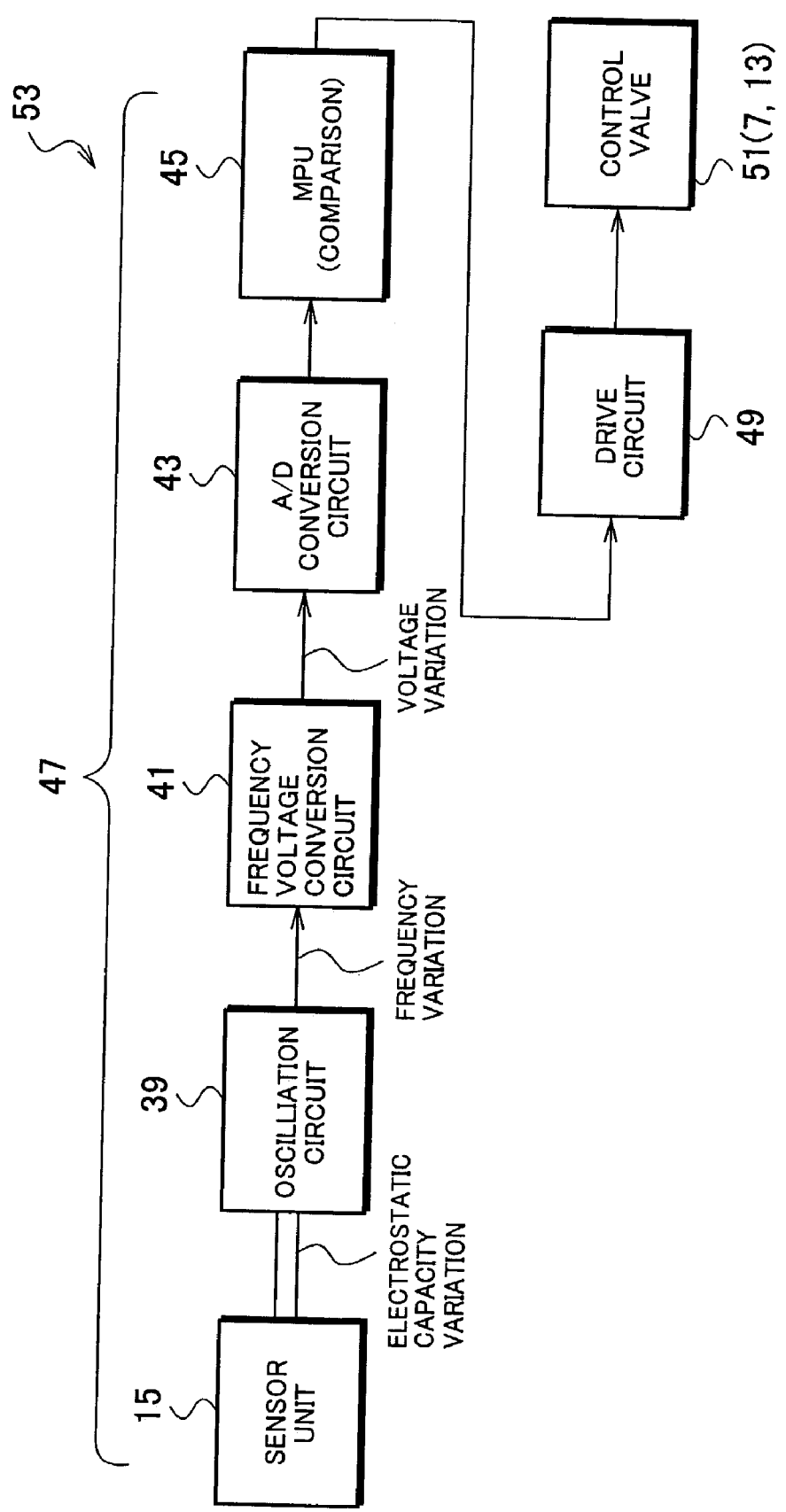
FIG. 9 is a block diagram of the piping fluid control system applying the capacitance sensor according to the embodiment.

FIG. 9 is a block diagram of the piping fluid control system 53 applying the capacitance sensor 15 according to this embodiment. A piping fluid decision device 47 includes the sensor unit 15, an oscillation circuit 39, a frequency voltage conversion circuit 41, an A/D conversion circuit 43, and an MPU 45. A piping fluid control system 53 is constituted with the piping fluid decision device 47, a drive circuit 49, and a control valve 51. The control valve 51 has first and second electromagnetic open-close valve 7 and 13 of FIG. 2. The MPU 45 constitutes a control means for controlling the control valve 51 as a adjust means.

In the MPU 45 is stored in advance a reference variation of capacitance of the path in the piping 1 when the fluid substance flows in the path. The reference variation of capacitance is used for a decision on a fluid condition, for example to be normal or abnormal, of the fluid substance flowing the path in the piping 1. In this embodiment, a variation of capacitance between when beer flowing the path in the piping 1 has a liquid state (to be normal) and when it has a froth state (to be abnormal) is stored as the reference variation of capacitance. Therefore, the MPU 45 in this embodiment constitutes a reference value storage means. A value of the reference variation of capacitance is arbitrarily adjustable in dependence such as on an amount of froth desired to be flown to the beer take-out machine 5 end. The MPU 45 adapted for comparing a detected variation of capacitance with the stored variation of capacitance to decide the fluid state of beer flowing in the path in the piping 1. Therefore, the MPU 45 in this embodiment also constitutes a fluid decision means.

When the sensor unit 15 detects a variation of capacitance, a frequency variation corresponding to the detected variation of capacitance from the oscillation circuit 39 to the frequency voltage conversion circuit 41. The frequency voltage conversion circuit 41 converts the input frequency variation into a voltage variation, and inputs the voltage variation to the A/D conversion circuit 43. The A/D conversion circuit 43 replaces the input voltage variation with a digital signal of a binary number value, and inputs the digital signal to the MPU 45. In this way, the detected variation of capacitance is inputted into the MPU 45. At MPU 45, the detected variation of capacitance is compared with stored reference variation of capacitance.

The MPU 45 depends on a result of the comparison to decide whether the fluid state of beer flowing in the path is a liquid or froth state, outputs this decision to the drive circuit 49. The drive circuit 49 controls the control valve 51 on the basis of the output from the MPU 45.

As shown FIG. 2, beer from the beer tank 3 flows inside the piping 1, and when this is sent to the beer take-out machine 5, a variation of capacitance of the path in the piping 1 is detected at the sensor unit 15. The first and second electromagnetic open-close valves 7 and 13 are controlled on the basis of this detection. While liquid beer is flowing in the piping 1, a variation of capacitance is little or less than a set value of the reference variation. Thus, a corresponding signal is sent from the MPU 45 via the drive circuit 49 to the first and second electromagnetic open-close valves 7 and 13, so that the first electromagnetic open-close valve 7 is opened and the second electromagnetic open-close valve 13 is closed. As the result, the system allows beer of a liquid state to be sent to the beer take-out machine 5.

On the other hand, if the beer flowing through the path in the piping 1 enters a froth state, a variation of capacitance exceeds the set value of the reference variation. Thus, a result of a detection by the sensor unit 15 is compared in the MPU 45, with a result, whereby a signal is output via the drive circuit 49 to the control valve, so that the first electromagnetic open-close valve 7 is closed and the second electromagnetic open-close valve 13 is opened.

As the result, the froth state beer flowing through the path in the piping 1 is wasted through the drain pipe 9 to the drain tank 11. By such control, it is ensured that liquid beer little of froth can be taken out from the beer take-out machine 5. Depending on a setting of a reference variation of capacitance at the MPU 45, the amount of froth mixed in liquid beer may be controlled to be taken out from the beer take-out machine 5, or the like.

The fluid state of the fluid substance flowing through the path in a piping 1 can be decided with non-contact manner, so that electrodes 33 and 35 are free from corrosion or such, permitting beer flowing in the piping 1 to be kept at a high sanitary condition. The variation of capacitance provides a great voltage variation, it, therefore, is unnecessary to integrate a detection result. Thus, it is allowing for a small calculation amount to perform a rapid and correct control, and permitting the system also to be compact.

The fluid state is detected by the variation of capacitance, so that it hardly receives influences of a magnetic field. Therefore, the sensor unit 15 can be disposed in, for example, a vicinity of the first electromagnetic open-close valve 7, this permits an increased design flexibility.

Figure 10:
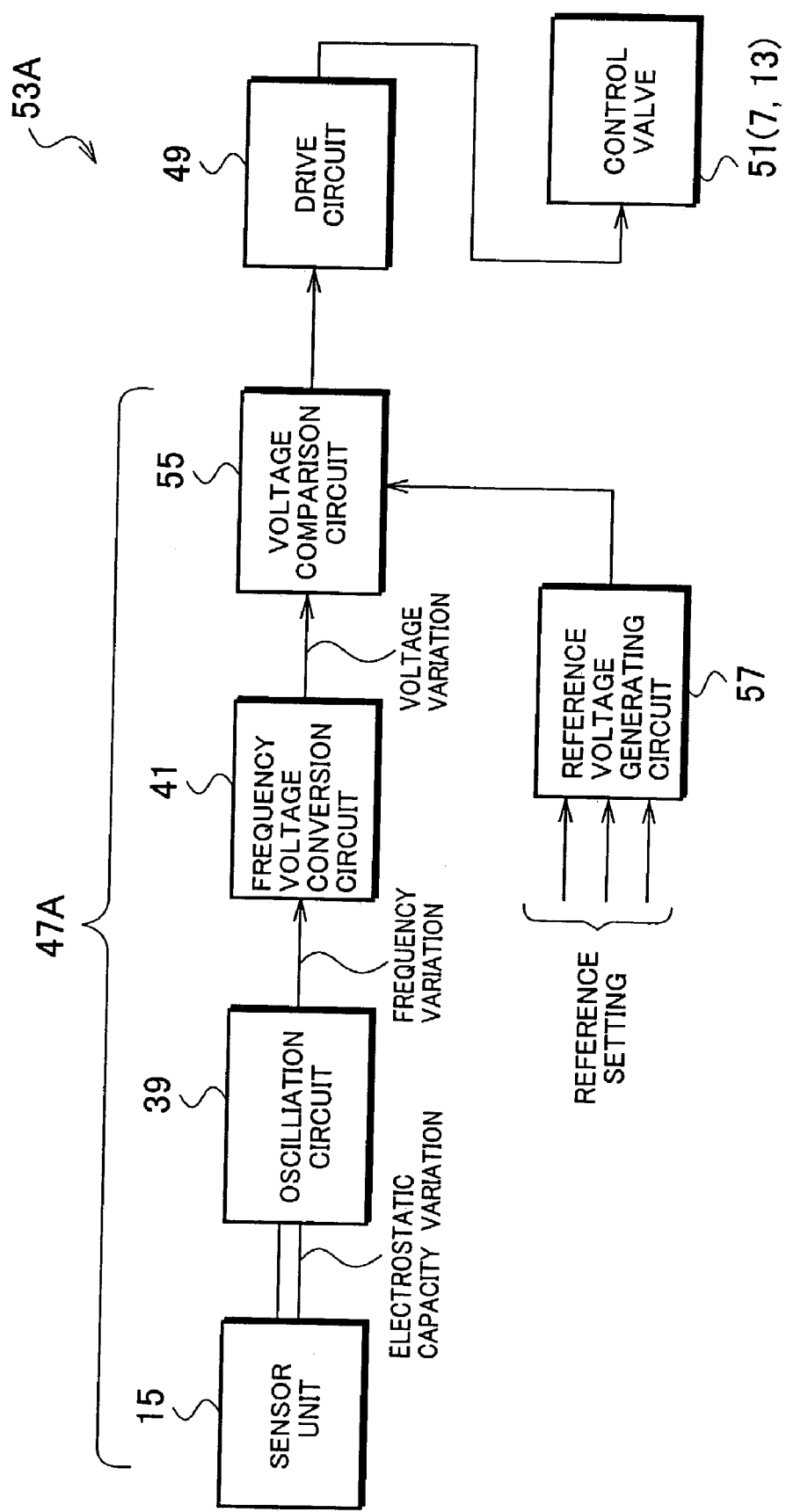
FIG. 10 is a block diagram of a piping fluid control system according to a modification of the embodiment.

FIG. 10 shows a piping fluid control system 53A according to a modification of the above embodiment. In FIG. 9, component parts corresponding to FIG. 8 are designated by like reference characters. The piping fluid control system 53A is provided with a voltage comparison circuit 55 and a reference voltage generating circuit 57 instead of the A/D conversion circuit 43 and the MPU 45 of FIG. 8.

A piping fluid decision device 47A includes a sensor unit 15, an oscillation circuit 39, a frequency voltage conversion circuit 41, the voltage comparison circuit 55, and the reference voltage generation circuit 57.

According to this embodiment, the reference voltage generating circuit 57 constitutes a reference value storage means. The reference voltage generation circuit 57 is for generating a reference voltage to be compared at the voltage comparison circuit 55. The reference voltage generation circuit 57 generates a reference voltage a reference voltage corresponding to a reference variation of capacitance to be set.

According to this embodiment, the voltage comparison circuit 55 constitutes a fluid decision means and control means. A reference voltage generated at the reference voltage generating circuit 57 is sent to the voltage comparison circuit 55, where it is compared with a voltage variation corresponding to a detected variation of capacitance. The voltage comparison circuit 55 outputs a signal on the basis of the comparison result, via a drive circuit 49 to a control valve 51.

Also, in this embodiment of FIG. 9, while the variation of capacitance is little or small, a first electromagnetic open-close valve 7 is opened and a second electromagnetic open-close valve 13 is closed. If the variation of capacitance exceeds a set value of the reference variation, the first electromagnetic open-close valve 7 is closed and the second electromagnetic open-close valve 13 is opened. Therefore, in the circuit arrangement of FIG. 9, beer can be securely sent to a beer take-out machine 5 when the state of beer flowing in a piping 1 is a liquid state, or securely wasted to a drain tank 11 when it is a froth state.

In above-described embodiments, although the drain pipe 9 as a branch pipe is connected between the sensor unit 15 and the first electromagnetic open-close valve 7, the first electromagnetic open-close valve 7 may be a 3-way valve and a drain pipe 9 may be connected to the 3-way valve. In this case, by a port-switching of the 3-way valve by way of an electrical switching control by a control means, a flow from the piping 1 to the beer take-out machine5 end and a flow from the piping 1 to the drain tank 11 end can be changed over.

In above-described embodiments, although the sensor unit 15 is fitted on the linear piping 1, the insulators 17 and 21 and the shield member 23 may be made of soft material, and the fitting may be performed to a piping 1 with a corner part or to the corner part with ease. In such a case, the spiral wounding of the electrode 19 allows an ensured arrangement of the electrode 19 along the corner part of the piping 1.

The electrodes 19 and 19A may be directly wound on the piping 1 made of insulating material such as a vinyl chloride pipe or the like, thereby eliminating the inner insulator 17.

In above-described embodiments, although beer is applied as fluid substance, any fluid substance else may be applied. For example, a liquid body as water or oil, a gaseous body such as air or carbon dioxide, or a plurality of solid bodies such as a metallic flow, a soil flow, a stone flow, or beans may be judged for the fluid state to perform a predetermined separation control or the like.

For example, in case of a cleaning of a food tank to be performed in order of a water cleaning, a hot water cleaning, a germicidal agent cleaning, or such, there may be stored as reference values in advance those variations of capacitance of a piping for sending them when water, hot water, a germicidal agent, or such flows therein. In a service a variation of capacitance in the piping may be detected by a sensor unit and compared with a reference value. Accordingly, it is ensured to judge which of the water, hot water, and the germicidal agent is used for a current cleaning of the tank. That is, the fluid state of fluid substance contains a change of kind of the fluid substance.

A plurality of branch pipes may be connected to a single piping, and the kind of a fluid substance may be detected by a variation of capacitance. Therefore, it is ensured to deliver a different kind of fluid substance from the piping to a respective branch pipe.

The decision by comparison of capacitance is considered to cover, not simply a comparison decision of its variation value, but also the capacitance itself to be within an equivalent scope.

What is claimed is:

1. A capacitance sensor for detecting a capacitance change in a path, comprising:
   a measuring electrode and a grounding electrode wound around the path; and
   the measuring electrode and the grounding being electrode paired with one another for sensing capacitance in conjunction with one another, the grounding electrode being narrower than the measuring electrode and spaced from the measuring electrode, the paired measuring and grounding electrodes being spirally wound around the path in a flow direction of the path.

2. The capacitance sensor of claim 1, further comprising a shield member covering the measuring electrode and the grounding electrode, and an insulator in between the shield member and the paired measuring electrode and grounding electrode.

3. The capacitance sensor of claim 2, wherein the measuring electrode and the grounding electrode are made of a conductive metallic film.

4. The capacitance sensor of claim 1, wherein the measuring electrode and the grounding electrode are made of a conductive metallic film.

* * * * *